(12) United States Patent
Michlitsch

(10) Patent No.: US 8,911,941 B2
(45) Date of Patent: Dec. 16, 2014

(54) METHODS AND APPARATUS FOR POINT-OF-CARE NUCLEIC ACID AMPLIFICATION AND DETECTION

(76) Inventor: Kenneth J. Michlitsch, Berwyn, PA (US)

(*) Notice: Subject to any disclaimer, the term of this patent is extended or adjusted under 35 U.S.C. 154(b) by 0 days.

(21) Appl. No.: 13/447,218

(22) Filed: Apr. 14, 2012

(65) Prior Publication Data
US 2012/0264116 A1    Oct. 18, 2012

Related U.S. Application Data

(60) Provisional application No. 61/475,257, filed on Apr. 14, 2011.

(51) Int. Cl.
| C12Q 1/68 | (2006.01) |
| C12P 19/34 | (2006.01) |
| C12M 1/36 | (2006.01) |

(52) U.S. Cl.
CPC ........................... *C12Q 1/6846* (2013.01)
USPC .................. 435/6.1; 435/91.2; 435/287.2

(58) Field of Classification Search
None
See application file for complete search history.

(56) References Cited

U.S. PATENT DOCUMENTS

| 5,411,876 | A | | 5/1995 | Bloch et al. |
| 5,498,392 | A | * | 3/1996 | Wilding et al. .............. 422/68.1 |
| 5,753,186 | A | * | 5/1998 | Hanley et al. ................. 422/550 |
| 2003/0013109 | A1 | * | 1/2003 | Ballinger et al. ................. 435/6 |
| 2005/0106713 | A1 | * | 5/2005 | Phan et al. ................. 435/287.2 |
| 2007/0141605 | A1 | * | 6/2007 | Vann et al. ......................... 435/6 |
| 2007/0292858 | A1 | * | 12/2007 | Chen et al. ......................... 435/6 |
| 2008/0176755 | A1 | * | 7/2008 | Amundson et al. ............... 506/7 |
| 2010/0015621 | A1 | * | 1/2010 | Chang et al. ....................... 435/6 |
| 2011/0294112 | A1 | | 12/2011 | Bearinger et al. |
| 2011/0294199 | A1 | | 12/2011 | Bearinger et al. |
| 2012/0202211 | A1 | * | 8/2012 | Ochoa Corona ............. 435/6.12 |

FOREIGN PATENT DOCUMENTS

WO    WO2009/018473 A1 *   2/2009

OTHER PUBLICATIONS

Jangam, S. R. et al., "Rapid, Point-of-Care Extraction of human immunodeficiency virus type 1 proviral DNA from whole blood for detection by real time PCR." Journal of Clinical Microbiology, Aug. 2009, vol. 47, No. 8, pp. 6363-2368.

Menassa, N. et al., "Rapid detection of fungal keratitis with DNA-stabilizing FTA filter paper." Investigative Ophthalmology and Visual Science, Apr. 2010, vol. 51, No. 4, pp. 1905-1910.

Weigl, B. H. et al., "Non-instrumented Nucleic-Acid Amplification Assay." Microfluidics, BioMEMS, and Medical Microsystems VI, Proc. of SPIE vol. 6886, 688604, 2008.

(Continued)

*Primary Examiner* — Betty Forman

(57) ABSTRACT

Methods and apparatus are provided for point-of-care nucleic acid amplification and detection. One embodiment of the invention comprises a fully integrated, sample-to-answer molecular diagnostic instrument that optionally may be used in a multiplexed fashion to detect multiple target nucleic acid sequences of interest and that optionally may be configured for disposal after one-time use. Optionally, sample preparation is fully or partially achieved via heat treatment and/or using a filter paper, such as a chemically treated filter paper, e.g., an FTA card. The instrument preferable utilizes an isothermal nucleic acid amplification technique, such as loop-mediated isothermal amplification (LAMP), to reduce the instrumentation requirements associated with nucleic acid amplification. Detection of target amplification may be achieved, for example, via detection of a color shift or fluorescence in a dye added to the amplification reaction.

15 Claims, 3 Drawing Sheets

(56) References Cited

OTHER PUBLICATIONS

LaBarre, P. et al., "Non-Instrumented Nucleic Acid Amplification (NINA): Instrument Free Molecular Malarai Diagnostics for Low-Resource Settings." 32nd Annual International Conference of the IEEE EMBS, Buenos Aires, Argentina, Aug. 31-Sep. 4, 2010. pp. 1097-1099.

Poon, L. L. M. et al., "Sensitive and Inexpensive Molecular Test for *falciparum* Malaria: Detecting *Plasmodium falciparum* DNA Directly for Heat-Treated Blood by Loop-Mediated Isothermal Amplification." Clinical Chemistry 52, No. 2, 2006, pp. 303-306.

Bearinger, J. P. et al., "Development and initial results of a low cost, disposable, point-of-care testing device for pathogen detection." IEEE Transactions on Biomedical Engineering, Mar. 2011, vol. 58, No. 3. pp. 805-808.

\* cited by examiner

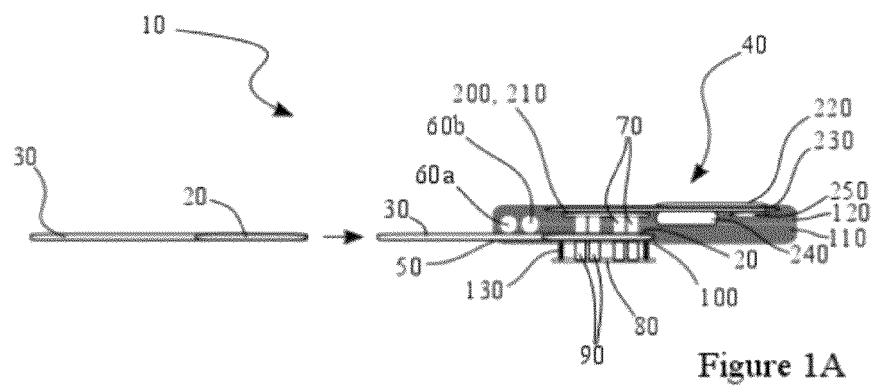
Figure 1A
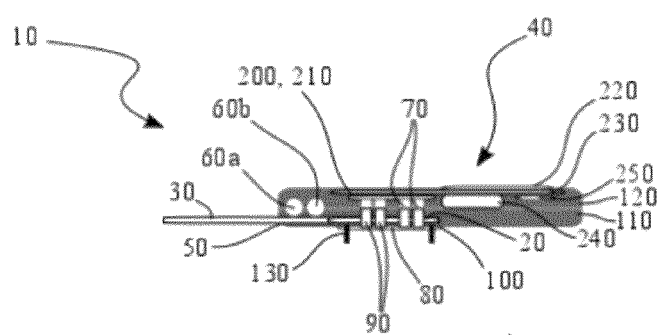
Figure 1B
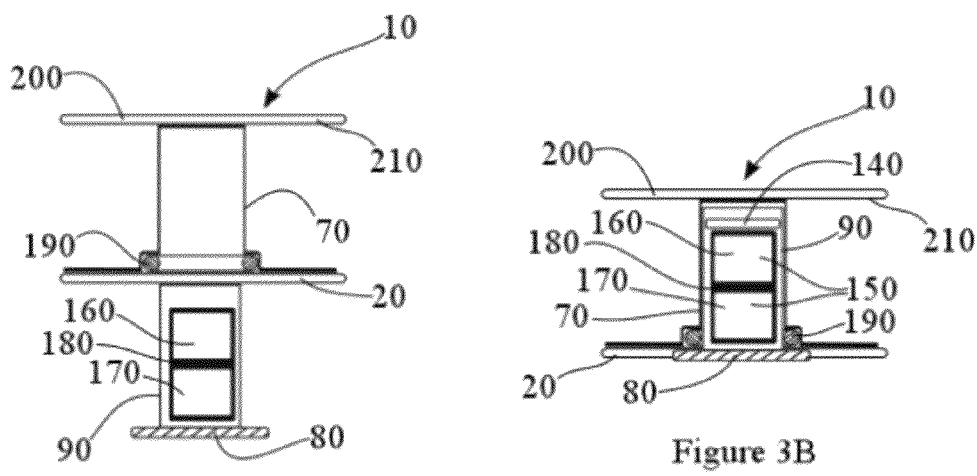
Figure 3A
Figure 3B

METHODS AND APPARATUS FOR POINT-OF-CARE NUCLEIC ACID AMPLIFICATION AND DETECTION

REFERENCE TO RELATED APPLICATIONS

The present application claims priority and the benefit of the filing date of U.S. provisional patent application Ser. No. 61/475,257, filed Apr. 14, 2011, which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and apparatus for nucleic acid amplification and detection. More particularly, the present invention relates to methods and apparatus for point-of-care nucleic acid amplification and detection.

BACKGROUND

Polymerase Chain Reaction (PCR) is considered the gold standard for nucleic acid amplification and detection because the specificity and sensitivity of PCR are considerably higher than that of analogous Enzyme-Linked Immuno-Sorbent Assay ("ELISA") tests. However, PCR systems are costly and require very clean samples. Point-Of-Care (POC) PCR systems generally are not fully disposable, are not appropriate for unskilled use, require substantial power and/or contain complicated microfluidic processing and readout. Thus, PCR traditionally has been limited to high resource, centralized laboratory settings.

In view of the foregoing, it would be desirable to provide methods and apparatus for point-of-care nucleic acid amplification and detection that overcome the drawbacks of previously known methods and apparatus.

BRIEF DESCRIPTION OF THE DRAWINGS

Several embodiments of the present invention will be apparent upon consideration of the following detailed description, taken in conjunction with the accompanying drawings, in which like reference characters refer to like parts throughout, and in which:

FIGS. 1A and 1B are schematic side-sectional views of apparatus for point-of-care nucleic acid amplification and detection, illustrating a method of use;

FIGS. 3A and 3B are detail side-sectional views of the apparatus of FIG. 1, illustrating a method of use;

DETAILED DESCRIPTION

Although this disclosure is detailed and exact to enable those skilled in the art to practice the disclosed technologies, the physical embodiments herein disclosed merely exemplify the various aspects of the invention, which may be embodied in other specific structures. While the preferred embodiments are described, the details may be changed without departing from the invention, which is defined by the claims.

FIGS. 1-3 illustrate one embodiment of fully integrated sample-to-answer molecular diagnostic apparatus 10 for point-of-care nucleic acid amplification and detection. Apparatus 10 may comprise a package size comparable to a digital home pregnancy test (e.g., a maximum dimension less than about 15 cm), a mass of less than about 150 g and/or a cost of production below about $10. The apparatus 10 optionally may be used in a multiplexed fashion to detect multiple target nucleic acid sequences of interest (e.g., to detect at least two target nucleic acid sequences of interest) and optionally may be configured for disposal after one-time use.

Preferably, sample preparation is fully or partially achieved using heat treatment and/or using a filter paper 20, such as a chemically treated filter paper, e.g., Flinders Technology Associates ("FTA") cards available from Whatman (Kent, UK). The apparatus preferable utilizes an isothermal nucleic acid amplification technique, e.g., loop-mediated isothermal amplification ("LAMP)", to reduce the instrumentation requirements associated with nucleic acid amplification. Detection of target amplification may be achieved, for example, via detection of a color shift and/or fluorescence in one or more dyes, such as hydroxynaphthol blue, picogreen, and/or SYBR green, added to the amplification reaction. Such colorimetric and/or fluorescent detection may be performed visually by an operator and/or may be achieved utilizing an imaging technique, such as spectrophotometric and/or fluorescence imaging, as described below.

As seen in FIGS. 1 and 2, apparatus 10 may comprise sample collector 30 including filter paper 20 (e.g., a chemically treated filter paper, such as an FTA card) onto which various sample matrices—including, but not limited to, food, urine, saliva, mucous, feces, blood, semen, tissue, cells, DNA, RNA, protein, plant matter, animal matter, solutions, solids, and other sample matrices—may be deposited (additional sample matrices will be apparent). In this manner, sample collector 30 may collect a sample S via filter paper 20.

In order to collect sample S with sample collector 30, filter paper 20 may, for example, be dipped or placed into one or more sample matrices of interest. Additionally or alternatively, one or more drops of one or more sample matrices of interest may, for example, be placed or deposited onto filter paper 20. Additionally or alternatively, filter paper 20 may, for example, be swabbed or wiped across one or more sample matrices of interest.

Figure 2A:
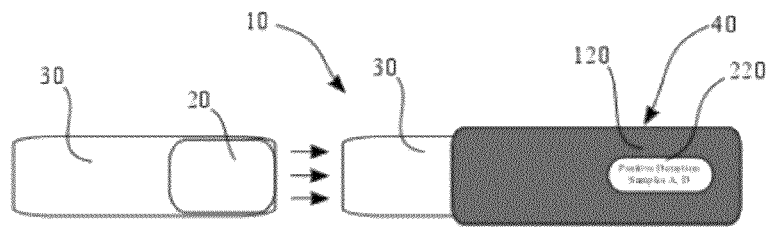
FIGS. 2A-2G are a top view and tear-down top views of the apparatus of FIG. 1, illustrating a method of use.

After collection of sample S, all or a portion of sample collector 30 and filter paper 20 may be inserted through insertion slot 50 into nucleic acid amplification instrument 40, as seen in FIGS. 1A and 2A. All or a portion of the sample collector 30 may, for example, be rigid or semi-rigid to facilitate insertion of paper 20 through slot 50 into instrument 40, though a flexible sample collector alternatively may be provided. Although, in the embodiment of FIGS. 1-3, sample collector 30 may be decoupled from instrument 40 during collection of sample S, it should be understood that sample collector 30 alternatively may be permanently or reversibly coupled to instrument 40 during collection of sample S (see, e.g., FIGS. 4-5). In some embodiments, sample collector 30 may be coupled to instrument 40 during collection of sample S, but may be configured to translate relative to instrument 40, such that sample collector 30 and paper 20 may be extended relative to instrument 40 to facilitate collection of sample S, then translated through slot 50 to insert paper 20 within instrument 40 after collection of the sample S.

Figure 2B:
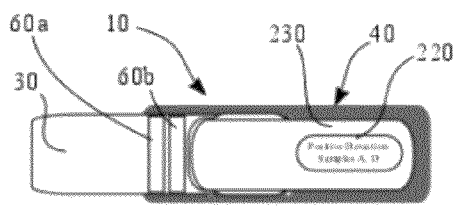

During insertion of paper 20 and sample collector 30 into instrument 40 of apparatus 10, filter paper 20 optionally may pass, contact and/or otherwise interact with one or more rollers, brushes, dispensers, sprayers or other elements 60 that prepare the sample for nucleic acid amplification by a skilled or unskilled practitioner. As seen in FIGS. 1 and 2B, sample preparation elements 60 may, for example, comprise one or more wash-dispensing elements 60A that apply a wash, such as purification reagent, to sample S as paper 20 passes, contacts and/or otherwise interacts with the wash-dispensing elements 60a during insertion of sample collector 30 into instrument 40. Additionally or alternatively, elements 60 may comprise one or more solution-dispensing elements 60b that apply a solution, such as a buffer solution (e.g., TE buffer) or rinse to sample S as paper 20 passes, contacts and/or otherwise interacts with the solution-dispensing elements 60b during insertion of sample collector 30 into instrument 40. During insertion of sample collector 30 into instrument 40, elements 60 may, for example, first apply a wash to sample S via element(s) 60a and then apply a buffer or rinse to sample S via element(s) 60b. In this manner, apparatus 10 may achieve sample preparation in a manner appropriate for either skilled or unskilled operation.

In addition or as an alternative to sample preparation element(s) 60, sample S may be prepared via heat treatment. For example, sample S may be heated to a temperature higher than required for isothermal amplification via LAMP (e.g., higher than about 60° C.-65° C.), thereby preparing the sample for LAMP via heat treatment. In some embodiments, sample S may comprise whole blood, which may, for example, be heat treated at about 99° C., e.g., for about 10 minutes, to achieve sample preparation. In some embodiments, sample S may not require preparation and/or placement of sample S on filter paper 20 may be sufficient to prepare the sample for nucleic acid amplification.

Figure 2C:
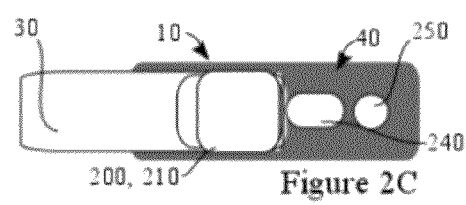
Figure 2D:
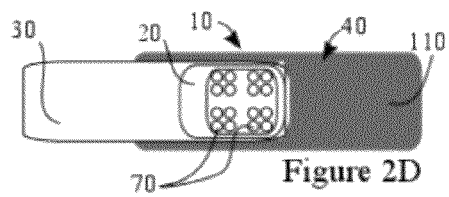
Figure 2E:
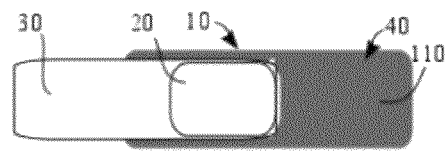
Figure 2F:
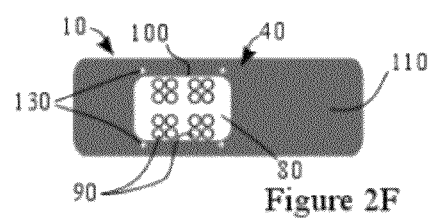

As seen in FIGS. 1A, 2D-2F and 3A, once sample collector 30 has been advanced into instrument 40, the collected and optionally prepared sample S on filter paper 20 may be positioned between multiple reaction chambers 70 and punch stage 80. Punch stage 80 comprises multiple punch elements 90 that are aligned with reaction chambers 70. As seen in FIGS. 1A, 2F and 3A, punch elements 90 are positioned below an opening or void 100 in bottom enclosure 110 of instrument 40. Bottom enclosure 110 may be coupled to top enclosure 120 in a manner that forms an outer casing or shell of instrument 40.

Punch stage 80 is configured to translate relative to linear bearings 130 attached to bottom enclosure 110. As seen in FIGS. 1B and 3B, translating punch stage 80 relative to linear bearings 130 advances punch elements 90 through the sample-containing filter paper 20 and into the aligned reaction chambers 70 (alternatively, reaction chambers 70 may be positioned within punch elements 90 after advancement of the punch elements through the paper 20), thereby positioning a punch 140 of sample-containing paper 20 within each reaction chamber 70. The surfaces of the reaction chambers 70 and punch elements 90 that are in proximity to paper 20 initially are open to facilitate such advancement of the punch elements into the reaction chambers. The punch elements and reaction chambers may, for example, comprise aligned cylinders or tubes.

As seen in FIG. 3, reagents 150 for conducting nucleic acid amplification (e.g., isothermal nucleic acid amplification) are positioned within each punch element 90 (alternatively or additionally, reagents 150 may be positioned within each reaction chamber 70). Reagents 150 may, for example, comprise enzyme 160 and master mix 170. When conducting nucleic acid amplification via LAMP, enzyme 160 may comprise Bst polymerase, while master mix 170 may, for example, comprise primers, buffer, $MgSO_4$, betaine and water.

Master mix 170 or enzyme 160 optionally also may comprise one or more dyes to facilitate detection of nucleic acid amplification. In some embodiments, master mix 170 may comprise a colorimetric dye, such as hydroxynaphthol ("HNB") blue. Detection of target amplification may be achieved, for example, via detection of a color shift in the colorimetric dye in the presence of amplicon, e.g., due to a shift in free magnesium ($Mg^{2+}$) concentration during LAMP amplification. Such colorimetric detection may be performed visually by an operator or may be achieved utilizing spectrophotometric imaging, as described below. In addition or as an alternative to colorimetric amplification detection with a colorimetric dye, a fluorescent dye, such as picogreen or SYBR green, may be utilized to detect amplification via fluorescence.

One or more of the reagents 150 optionally may be lyophilized, e.g., to facilitate long-term storage. Additionally or alternatively, one or more of the reagents may be temporarily sequestered from one or more of the other reagents prior to nucleic acid amplification via instrument 40. Such temporary reagent sequestration may facilitate long-term storage of the reagents and/or may forestall reagent mixing (and, thus, nucleic acid amplification) until desired, e.g., until the reagents have been exposed to sample S. For example, enzyme 160 may be sequestered from master mix 170, as shown in FIG. 3 (though it should be understood that one or more additional or alternative reagents 150 may be sequestered from one or more of the other reagents 150).

In some embodiments, one or more of the reagents 150 (e.g., enzyme 160) may be temporarily sequestered within one or more temporary sequestration vessels 180 (see FIG. 3). In some embodiments, temporary sequestration vessel(s) 180 may, for example, comprise one or more thermal encasement materials that are configured to melt, become porous or otherwise release the sequestered reagent(s) 150 upon heating, e.g., during nucleic acid amplification. The thermal encasement material(s) may, for example, comprise polycaprolactone, and/or phase change materials such as paraffin or wax. In some embodiments, temporary sequestration vessel(s) 180 may comprise one or more blister packs or other containers such as gel caps that may be punctured or otherwise opened (e.g., via punch elements 90 during translation of punch stage 80) to release the sequestered reagent(s) 150. When vessel(s) 180 comprise gel caps, they optionally may be opened via hydrolysis in addition or as an alternative to puncturing.

As best seen in FIG. 3B, translation of punch stage 80 positions a punch element 90, including prepared sample-containing filter paper punch 140 and reagents 150, within each reaction chamber 70. The punch elements 90 optionally are sized or geometrically shaped such that they friction (or otherwise) lock within the reaction chambers 70 after advancement into the chambers 70. Each reaction chamber 70 and/or punch element 90 may comprise a mechanical gasket 190, such as an O-ring, that ensures a fluid tight seal of each punch element 90 within each reaction chamber 70 after punching of the sample-containing filter paper 20.

Upon establishment of fluid tight seal, each reaction chamber 70 with sample-containing punch 140 and reagents 150 is configured to amplify a nucleic acid target sequence of interest, if contained in the sample S. Different chambers 70 may utilize different primers to facilitate amplification and detection of different target sequences of interest (i.e., to facilitate multiplexed nucleic acid amplification and detection). A fraction of the chambers 70 may serve as positive controls. Additionally or alternatively, a fraction of the chambers 70 may serve as negative controls. Negative and/or positive control chambers 70 optionally may be pre-sealed prior to sealing of the remaining chambers 70 with sample-containing punches 140. Negative control chambers 70 may not comprise punches 140 or may comprise punches 140 that contain no sample S. Positive control chambers 70 may contain one or more target nucleic acid sequences of interest that are expected to amplify during nucleic acid amplification (e.g., the positive control chambers may comprise punches 140 containing the one or more target nucleic acid sequences of interest).

In the manner described above, each (non-control) reaction chamber 70 may be loaded and sealed with (an optionally prepared) sample-containing filter paper punch 140 and reagents 150, thereby facilitating nucleic acid amplification, e.g., isothermal nucleic acid amplification. The loaded and sealed chambers 70 may be heated, e.g., isothermally heated, to amplify the one or more target nucleic acid sequences of interest. When conducting isothermal amplification via LAMP, the contents of chambers 70 may be heated in the range of about 60° C.-65° C. for about 15-70 minutes. Such heating may be achieved via a healing element utilizing any of variety of techniques, including (but not limited to) electrical, chemical and electrochemical techniques. For example, chambers 70 may be resistively heated via a hearing element, e.g., via a coating on an imaging sensor as described below.

As discussed previously, detection of target amplification optionally may be achieved via detection of a color shift (i.e. a wavelength shift) and/or fluorescence (i.e., an intensity shift) in one or more dyes in the presence of amplicon. Such colorimetric and/or fluorescence detection may be performed visually by an operator and/or may be achieved utilizing an imaging technique, such as spectrophotometric and/or fluorescence imaging. In the embodiment of FIGS. 1-3, sensor 200, such as spectrophotometric CMOS or CCD imaging sensor 200, is in proximity to reaction chambers 70 for detection of a color shift, fluorescence or some other visible change indicative of target nucleic acid sequence amplification (see, e.g., FIGS. 1 and 2C). Reaction chambers 70 (see FIG. 3) preferably are transparent to facilitate detection of visible changes within the reaction chambers.

Sensor 200 optionally may comprise coating 210, such as Indium Tin Oxide ("ITO") coating 210, which may be utilized to resistively heat the contents of each reaction chamber 70 to achieve target nucleic acid amplification. As discussed previously, when conducting isothermal amplification via LAMP, the contents of chambers 70 may be heated in the range of about 60° C.-65° C. for about 15-70 minutes. When one or more of the reagents 150 are sequestered in one or more temporary sequestration vessels 180 that comprise one or more thermal encasement material(s), the vessel(s) 180 may partially or completely melt, become more porous or otherwise release the sequestered reagents 150 (e.g., release sequestered enzyme 160) upon heating with ITO coating 210. After release of the sequestered reagent(s) 150 from the vessel(s) 180, all of the reagents 150 (including enzyme 160 and master mix 170), mix with each other in the presence of sample-containing filter paper punch 140, and isothermal amplification proceeds.

Imaging sensor 200 may measure a baseline color of reagents 150 prior to isothermal heating and a final color of the reagents after isothermal heating (e.g., after isothermal heating via ITO coating 210). Since the reagents 150 within each reaction chamber 70 may, for example, include a colorimetric (or fluorescent) dye that shifts in color, e.g., from purple to blue, upon amplification of a target nucleic acid sequence, any such shift in color within the reaction chambers may be detected by the imaging sensor 200 as a differential between the baseline and final color, and this differential may be indicative of target amplification. As seen in FIGS. 1 and 2A-2B, digital readout or display 220 may output detection results (and/or instructions) to the user, removing any risk of ambiguity. While the embodiment of FIGS. 1-3 (and of FIGS. 4-5) illustratively achieves colorimetric or fluorescence detection via spectrophotometric imaging, it should be understood that such colorimetric or fluorescence detection additionally or alternatively may be performed visually by an operator.

As seen in FIGS. 1 and 2C, instrument 40 may comprise a logic chip 230 for controlling the operation of sensor 200, for controlling nucleic acid amplification via heating of chambers 70 (e.g., via sensor coating 210), for comparing baseline and final color measurements taken with sensor 200 to determine whether amplification has occurred, and/or for controlling the display of instructions or detection results via display 220. Wires and/or circuit board 240 (see FIGS. 1 and 2B) may connect the logic chip 230 to sensor 200 with coating 210, to display 220 and to a power supply 250. Power supply 250 may, for example, comprise one or more batteries, such as one or more button-cell batteries (see FIGS. 1 and 2C) for powering instrument 40. Instrument 40 may, for example, be powered for one-time, disposable use.

Instrument 40 may automatically initiate nucleic acid amplification and detection upon sealing of chambers 70 with punches 140. For example, translation of punch stage 80 and/or sealing of chambers 70 may complete a circuit that activates logic chip 230. Additionally or alternatively, the user or operator of instrument 40 may initiate nucleic acid amplification and detection, e.g., via an on/off switch, button, toggle, etc.

FIG. 2 provide top and teardown top views of apparatus 10 prior to translation of punch stage 80 and approximation of punch elements 90 with reaction chambers 70. FIG. 2A illustrates insertion of sample collector 30 with filter paper 20 into instrument 40 of fully assembled apparatus 10. In FIG. 2B, top enclosure 120 of instrument 40 has been removed, exposing optional sample preparation elements 60 comprising wash-dispensing element 60a and solution-dispensing element 60b, digital display 220 and circuit board 230. In FIG. 2C, the digital display and circuit board have been removed, exposing sensor 200 with coating 210, logic chip 240, power supply 250 and bottom enclosure 110. In FIG. 2D, the sensor, logic chip and power supply have been removed, exposing reaction chambers 70 and sample collector 30 with filter paper 20 (e.g., chemically treated filter paper, such as an FTA card) on which sample S may be placed. In FIG. 2E, the reaction chambers have been removed, fully exposing the sample collector 30 and filter paper 20. In FIG. 2F, the sample collector and filter paper have been removed, exposing void or opening 100 in bottom enclosure 110, as well as linear bearings 130.

Figure 2G:
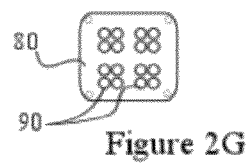

Punch elements 90 and punch stage 80 can be seen in FIG. 2F through void 100. Mechanical gaskets 190 (e.g., O-rings) may be attached to punch elements 90 and/or to chambers 70. In FIG. 2G, the bottom enclosure and linear bearings have been removed, exposing punch elements 90 and punch stage 80. Punch elements 90 may contain reagents 150. One or more of the reagents 150 may be lyophilized and/or may be sequestered within one or more temporary sequestration vessel(s) 190.

Figure 4:
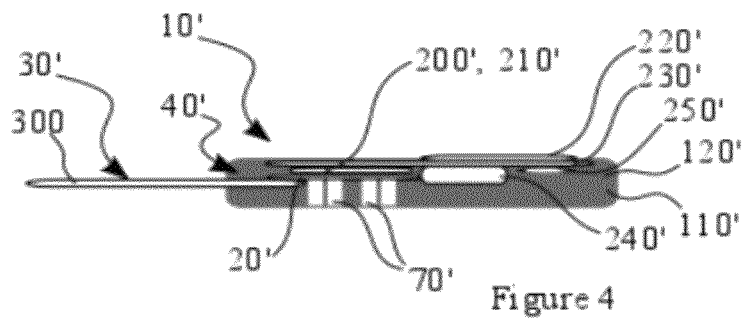
FIG. 4 is a side-sectional view of another embodiment of the point-of-care nucleic acid amplification and detection methods and apparatus of FIGS. 1-3.

The methods and apparatus of FIGS. 1-3 provide fully contained, sample-to-answer, nucleic acid sample preparation, (optionally multiplexed) target amplification and detection in (an optionally disposable, e.g., single use disposable) instrument 40 that is appropriate for use in limited resource settings at the point of care by relatively unskilled users. FIGS. 4 and 5 provide another embodiment of (optionally disposable) point-of-care nucleic acid sample preparation, target amplification and detection methods and apparatus. In the embodiment of FIGS. 4 and 5, sample collector 30' of apparatus 10' comprises lateral flow strip 300, which optionally may be impregnated with, or otherwise incorporate, lysis chemicals. Optionally, sample collector 30' may be permanently attached to the rest of instrument 40'. Optionally, sample collector 30' may be configured to translate relative to instrument 40'. Filter paper 20' (e.g., chemically treated filter paper 20', such as an FTA card), is integrated into instrument 40' and is in fluid contact with lateral flow strip 300 of sample collector 30'. The embodiment of FIGS. 4 and 5 may, for example, be appropriate for use with urine samples in a manner akin to home pregnancy test kits.

Figure 5A:
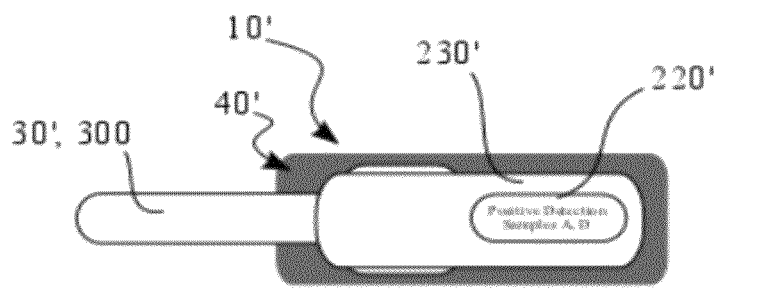
FIGS. 5A-5C are tear-down top views of the apparatus of FIG. 4, illustrating a method of use.
Figure 5B:
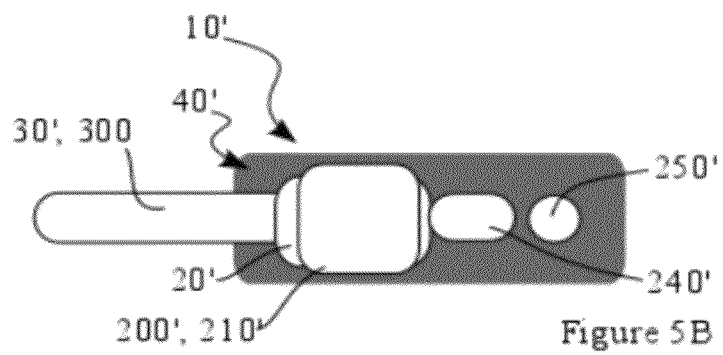
Figure 5C:
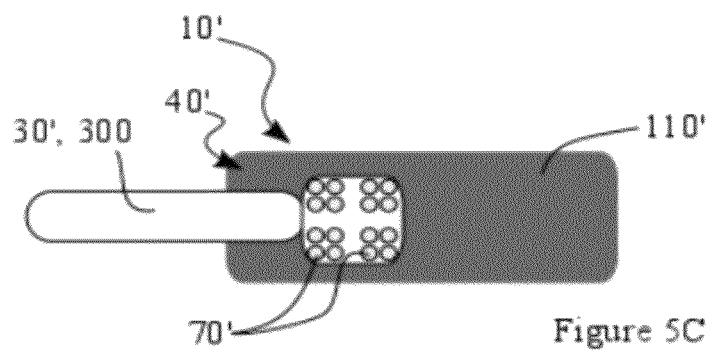

FIG. 5 provide teardown top views of apparatus 10'. In FIG. 5A, top enclosure 120' of instrument 40' has been removed, exposing digital display 220' and circuit board 230'. In FIG. 5B, the digital display and circuit board have been removed, exposing sensor 200' with coating 210', filter paper 20', logic chip 240' and power supply 250'. Filter paper 20' is in fluid communication with lateral flow strip 300 of sample collector 30'. In FIG. 5C, the sensor, filter paper, logic chip and power supply have been removed, exposing reaction chambers 70'.

CONCLUSION

Although preferred illustrative embodiments of the present invention are described above, it will be apparent to those skilled in the art that various changes and modifications may be made thereto without departing from the invention. It is intended in the appended claims to cover all such changes and modifications that fall within the true spirit and scope of the invention.

What is claimed is:

1. A method for point-of-care amplification and detection of a target nucleic acid sequence, the method comprising:
   collecting a sample matrix with filter paper;
   advancing a punch element through the filter paper to form at least one punch of the filter paper;
   transferring the at least one punch of the filter paper to a reaction chamber comprising nucleic acid amplification reagents;
   sealing the at least one punch of the filter paper within the reaction chamber in fluid communication with the nucleic acid amplification reagents;
   heating the nucleic acid amplification reagents with a heating element in order to amplify the target nucleic acid sequence when contained within the sample matrix;
   detecting amplification of the target nucleic acid sequence with a sensor;
   displaying detection results obtained with the sensor on a display; and
   disposing of the at least one punch of the filter paper, the reaction chamber, the heating element, the sensor, the display and the nucleic acid amplification reagents after one-time use.

2. The method of claim 1, wherein the filter paper further comprises chemically treated filter paper that at least partially prepares the sample matrix for nucleic acid amplification.

3. The method of claim 1, wherein heating further comprises isothermally heating.

4. The method of claim 1 wherein detecting further comprises detecting with an imaging sensor.

5. The method of claim 1, wherein detecting comprises detecting changes in a dye that are induced by amplification of the target nucleic acid sequence.

6. The method of claim 1, wherein collecting further comprises collecting with a lateral flow strip.

7. The method of claim 1 further comprising preparing the sample matrix for nucleic acid amplification before amplifying.

8. The method of claim 7, wherein preparing further comprises heating the sample matrix.

9. The method of claim 7, wherein preparing further comprises preparing the sample matrix with lysis chemicals.

10. The method of claim 1 further comprising temporarily sequestering at least one nucleic acid amplification reagent prior to amplifying.

11. The method of claim 10 further comprising releasing the at least one temporarily sequestered nucleic acid amplification reagent prior to heating.

12. The method of claim 10, wherein heating further comprises releasing the at least one temporarily sequestered nucleic acid amplification reagent from within a thermal encasement material by melting the thermal encasement material.

13. The method of claim 1 further comprising conducting experimental controls.

14. The method of claim 13 further comprising disposing of the experimental controls after one-time use.

15. The method of claim 1, wherein the target nucleic acid sequence further comprises multiple target nucleic acid sequences.

* * * * *